United States Patent [19]

Bossart et al.

[11] Patent Number: 4,799,374

[45] Date of Patent: Jan. 24, 1989

[54] LIQUID SEPARATOR

[75] Inventors: Clayton J. Bossart, Monroeville; Glenn H. Fertig, Natrona Heights; Albert L. Welker, Pittsburgh, all of Pa.

[73] Assignee: Mine Safety Appliances Company, Pittsburgh, Pa.

[21] Appl. No.: 120,131

[22] Filed: Nov. 13, 1987

[51] Int. Cl.⁴ .................. G01N 33/497; G01N 21/84
[52] U.S. Cl. .................. 73/1 G; 73/863.01; 73/863.02; 73/863.23; 128/719; 250/343
[58] Field of Search ............. 73/1 G, 863.23, 863.24, 73/863.01, 863.02, 863.03, 864.34, 864.73, 863.21; 250/338.1, 343, 338.5; 128/719, 730

[56] References Cited

U.S. PATENT DOCUMENTS

| 3,566,865 | 3/1971 | Hay | 73/1 G X |
| 3,976,450 | 8/1976 | Mercote et al. | 73/1 G X |
| 4,094,187 | 6/1978 | Naverre, Jr. | 73/1 G |
| 4,267,721 | 5/1981 | Longenecker et al. | 73/1 G |
| 4,509,359 | 4/1985 | Gedeon et al. | 73/1 G X |
| 4,516,424 | 5/1985 | Rowland | 73/1 G X |
| 4,680,956 | 7/1987 | Huszczuk | 73/1 G |

FOREIGN PATENT DOCUMENTS 2455977  8/1976  Fed. Rep. of Germany ...... 250/343

Primary Examiner—Tom Noland

[57] ABSTRACT

A liquid separator for removing liquid from a breath sample comprises a liquid trap having a conduit passing the breath sample and opening through a check valve to reservoir chamber. Sample flow is diverted to the reservoir and ambient air is drawn back through the conduit and check valve to backflush liquid in the conduit to the reservoir. The reverse flow is activated by the presence of liquid in the sample line, periodically actuated by a timer or both. The reverse air flow may be used as a zero calibration gas for an infrared analyzer.

4 Claims, 2 Drawing Sheets

LIQUID SEPARATOR

FIELD OF THE INVENTION

This invention relates to liquid separators and more particularly to separators for removing liquid from breath samples and breath analyzer systems incorporating the liquid separators.

BACKGROUND OF THE INVENTION

Gas analyzers are used to measure gases exhaled by a patient. In particular, carbon dioxide is monitored to determine the physiology of a patient. This is of prime importance during and immediately after surgery, and during respiration therapy. A major problem area in the analysis is the removal of entrained liquid either from the patient or the condensation from the breath or humidified oxygen supplied by a ventilator. This problem is further complicated by the need for rapid pneumatic response time, so that the visual waveform of the patient's exhaled $CO_2$ displayed electronically on a breath-by-breath basis will be faithfully reproduced. Any large and/or dead volumes anywhere in the sample train can cause mixing of the gas and tend to integrate rapid peaks and ultimately degrade the waveform.

Filters have heretofore been used in breath sampling lines, such as hydrophobic membranes (U.S. Pat. No. 4,558,708), sintered metal (U.S. Pat. No. 4,558,709) and water absorbents (U.S. Pat. No. 4,446,869). Such filters, however, become saturated and must be changed over extended sampling periods. Mechanical liquid traps in which liquid is collected in a reservoir have greater liquid capacity, see, for example, U.S. Pat. No. 4,579,568, but the increased volume of the system increases response time and convection or diffusion of the gas from the liquid reservoir dilutes the breath sample.

SUMMARY OF THE INVENTION

It is an object of this invention to provide a liquid separator that effectively separates liquid from a breath sample to be analyzed without significantly degrading pneumatic response time. Another object of the invention is to provide a breath sampling system that permits accurate waveform analysis over a breathing cycle. A further object is to provide a breath sampling system that has a minimum volume when sampling and that provides an isolated reservoir for collection of entrained liquid.

The liquid separator comprises a liquid trap having a substantially horizontal conduit with an inlet and an outlet, a reservoir chamber, a bottom outlet from the conduit opening to the reservoir chamber, a one-way valve means closing said bottom outlet and permitting flow only from the conduit to the reservoir chamber; means to the flow the breath sample through the conduit; and means to divert the sample flow to the reservoir chamber and flow air back through the outlet and the bottom outlet to the reservoir chamber whereby liquid is backflushed from the conduit to the reservoir chamber.

The means to divert the sample flow and back-flow air back through the outlet may be responsive to the presence of liquid in the sample line, or periodically activated by a timer, or both. When using an infrared $O_2$ analyzer, the reverse air flow, freed of $CO_2$, is used as a zero calibration gas.

DETAILED DESCRIPTION OF THE PREFERRED EMBODIMENTS

Figure 1:
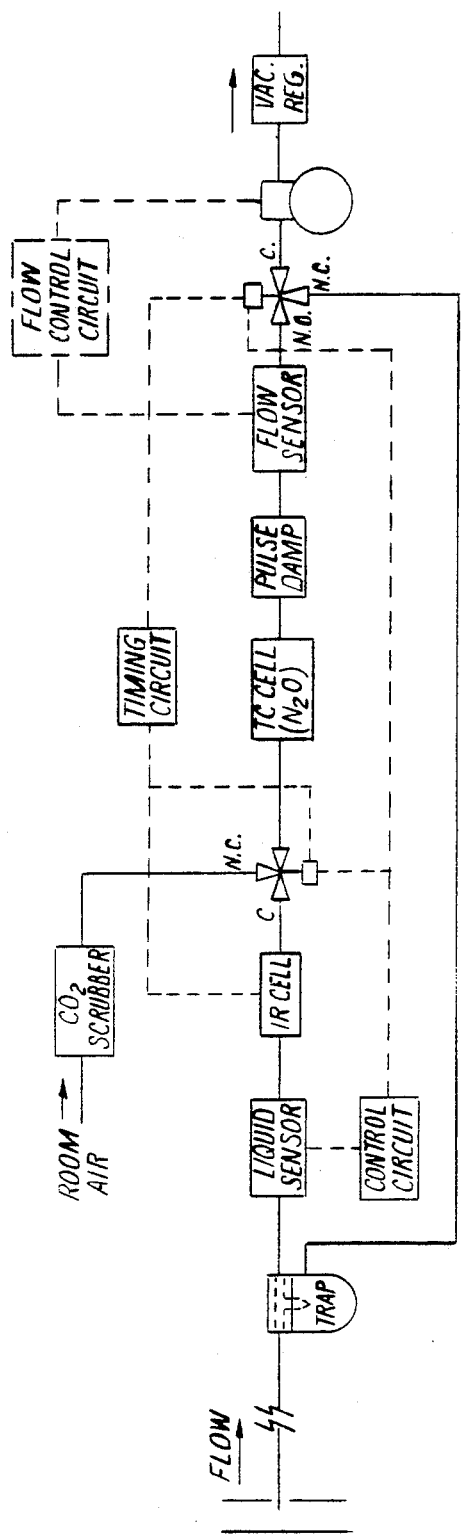
FIG. 1 is a Flow Diagram of a breath analyzer system in accordance with this invention.
Figure 2:
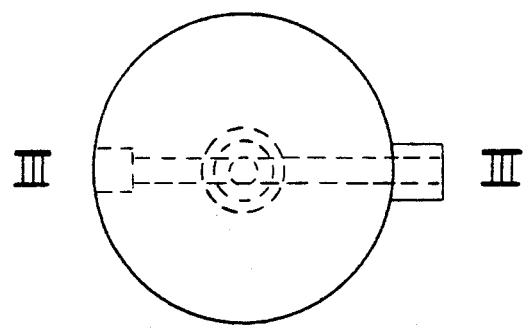
FIG. 2 is a plan view of the liquid trap of FIG. 1.
Figure 3:
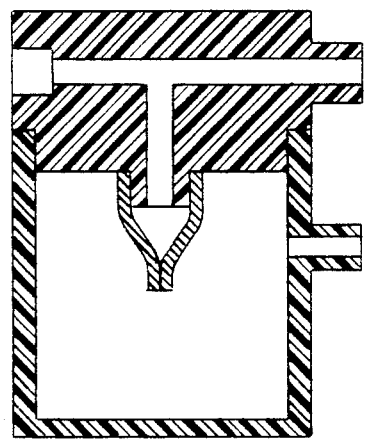
FIG. 3 is a sectional view on line III—III of FIG. 2.

Referring to FIG. 1, small diameter tubing 2 is connected to cannula or airway 4 and subjected to a vacuum drawn by diaphragm pump 6 to withdraw the breath sample from the airway. Tubing 2 is connected to inlet 8 of liquid trap 10, shown in detail in FIG. 2 and FIG. 3.

The trap has a cover member 12 with a horizontal bore 14 therethrough forming inlet 8 to accept a luer-loc fitting and outlet 16. Vertical bore 18 opens the bottom of bore 14 to chamber 20, formed by the cover and cup-shaped housing 21 which are sealed together by friction fit or threads. Bore 18 is closed by a duckbill check valve 22 supported by integral sleeve 24. The check valve may be a Model VA 3143 of silicone rubber available from Vernay Laboratories. Outlet 26 is connected to a normally closed port of solenoid valve 28.

Figure 4:
FIG. 4 is a sectional view of the liquid trap of FIG. 1.

Outlet 16 from the liquid trap is connected through a length 29 of per fluorinated ion exchange polymer tubing, such as Nafion ® tubing, to a liquid sensor 32. As is well known, water, but not gas, will be absorbed and pass through the wall of the Nafion tubing to the drier ambient air removing some moisture from the breath sample. A preferred liquid sensor of minimal volume, shown in FIG. 4, consists of two metal tubes 34, 34a, separated by a gap 36 and held in place by insulating tubing 38. Tubes 34 and 34a are connected by leads 40 and 42 to a control circuit 44 that is responsive to a change in resistance resulting from water droplets bridging gap 36 and operates solenoid valves 28 and 46.

The liquid sensor outlet is connected by tubing to the inlet of an infrared analyzer cell or other anayltical device for measuring carbon dioxide or other gas component of the breath sample. The cell outlet is connected to solenoid 3-way valve 46 through a common port to a normally open port and a normally closed port openable to the ambient air through $CO_2$ scrubber 48. The normally open port of valve 46 is connected through an optional second analytical device 50, a pulse damper 52, a flow sensor 54, and solenoid valve 28, to pump 6.

The second analytical device may be a thermal conductivity cell for measuring $N_2O$ when the patient is being given $N_2O$ anesthesia or other analytical device which is not subjected to back flushing. The pulse damper may be a small chamber with a flexible wall. The flow sensor may be a conventional hot wire miniaturized mass flowmeter connected to a null balance bridge flow control circuit 56, that regulates the speed of pump 6 to provide constant flow. Water droplets in the patient sample line will increase the resistance to flow, but this resistance is overcome to provide a constant flow through the analytical device by increasing the pump speed.

In the normal sample mode, the breath sample is drawn through the trap, Nafion tubing, liquid sensor, analytical devices and the normally open solenoid valves. The system provides a minimum volume between the sampling point and the infrared analyzer cell, so response time is fast to produce an accurate waveform analysis of $CO_2$ over the entire breathing cycle. The effective volume of the liquid trap is only the volume of the bores 14 and 18 and check valve 12, inasmuch as the chamber 20 is isolated from the breath sample by valve 12. This effective volume can be as little as about 150 microliters, for example, in a typical trap one inch in diameter with 1/16-inch bores. The dead volume not directly in the flow path, i.e. the volume of bore 18 and the duckbill valve 22, is only about 20 microliters.

Liquid that passes the trap and perfluorinated tube 30 will form droplets in the liquid sensor, reducing the resistance across tubes 34 and 34a and activating the control circuit to open the normally closed ports and close the normally open ports of the solenoid valves. In this liquid removal mode, ambient air is drawn by pump 6 in a reverse direction through solenoid valve 46, the infrared analyzer cell, the liquid sensor, and the trap outlet, and through valve 22 to the reservoir chamber 20. Thus liquid is prevented from entering and damaging the analyzer cell or causing inaccurate readings. The vacuum created in the reservoir by this action also serves to maintain flow from the patient sampling line through the duckbill valve 12, thus ensuring a fast, updated breath sample on return to the normal mode. This operation also does not allow back flushed air to reach the patient airway. In the liquid removal mode the flow sensor sees no flow, resulting in the pump operating at full capacity.

Timing circuit 58 periodically activates the solenoid valves to operate the system in the liquid removal mode in synchronization with a zero calibration cycle of the infrared analyzer. Any $CO_2$ in the ambient air is removed by scrubber 48, providing a $CO_2$-free calibration gas for the infrared analyzer. A calibration procedure by which both zero and span are calibrated with $CO_2$-free air is described in the copending application, Ser. No. 07/047,650, of common ownership with the application.

A vacuum regulator 60 downstream of the pump allows the exhausted sample to be vented to a hospital scavenger system. The regulator renders the $CO_2$ sampling system immune to variations of vacuum in the scavenger system.

We claim:

1. A breath sampling system for measuring $CO_2$ in exhaled breath comprising:
    a sampling conduit opening to an airway and a liquid trap having a substantially horizontal conduit with an inlet and an outlet, a reservoir chamber, a bottom outlet from the conduit opening to the reservoir chamber, a one-way valve means closing said bottom outlet and permitting flow only from the conduit to the reservoir chamber,
    a liquid sensor having an outlet and an inlet interconnected by perfluorinated tubing to the trap outlet,
    an infrared analyzer cell responsive to $CO_2$ having an outlet and an inlet connected to the liquid sensor outlet,
    means to provide a constant flow through the liquid trap, liquid sensor and analyzer cell,
    means responsive to the presence of liquid in the liquid sensor to direct the sample flow to the reservoir chamber and flow ambient air in a reverse direction through the analyzer cell and the liquid sensor to the reservoir.

2. A breath sampling system according to claim 1 comprising means to remove $CO_2$ from the ambient air.

3. A breath sampling system according to claim 2 comprising second means to direct the sample flow to the resevoir chamber and flow ambient air in a reverse direction through the analyzer cell and the liquid sensor to the reservoir, the second means becoming operative periodically to provide zero gas to the analyzer cell.

4. A breath sampling system for measuring $CO_2$ in exhaled breath comprising:
    an infrared analyzer cell responsive to $CO_2$,
    a sampling conduit opening to an airway,
    a pump and means interconnecting the cell, conduit and pump to flow a breath sample through the cell,
    and means periodically closing the sample conduit from the pump and opening the pump to ambient air from which $CO_2$ has been removed,
    whereby ambient air zero gas is periodically flowed through the cell.

* * * * *